United States Patent [19]

Watanabe

[11] Patent Number: 4,547,067
[45] Date of Patent: Oct. 15, 1985

[54] APPARATUS FOR DETECTING FAULTS IN TRANSPARENT OBJECTS

[75] Inventor: Tsukasa Watanabe, Kobe, Japan

[73] Assignee: Yamamura Glass Kabushiki Kaisha, Hyogo, Japan

[21] Appl. No.: 560,966

[22] Filed: Dec. 13, 1983

[30] Foreign Application Priority Data

Dec. 21, 1982 [JP] Japan .................. 57-225443

[51] Int. Cl.⁴ .................. G01B 11/18; G01N 21/04
[52] U.S. Cl. .................. 356/239; 356/33; 356/240; 250/223 B
[58] Field of Search .................. 356/33, 35, 239, 240, 356/432; 250/223 B, 572

[56] References Cited

U.S. PATENT DOCUMENTS

| | | |
|---|---|---|
| 3,411,009 | 11/1963 | Ford et al. .................. 250/223 |
| 3,727,068 | 4/1973 | Poynton et al. .................. 250/220 M |
| 3,811,775 | 5/1974 | Abu-Saud .................. 356/35 |
| 3,963,348 | 6/1976 | Nakatani et al. .................. 356/33 |
| 4,280,624 | 7/1981 | Ford .................. 209/524 |

*Primary Examiner*—John E. Kittle
*Attorney, Agent, or Firm*—Holman & Stern

[57] ABSTRACT

In a detecting system adapted to detect foreign matters as faults of a glass bottle, between a projection path of a diffused light towards the object to be inspected and said object, a plane polarizing plate of a circular polarizer which includes the plane polarizing plate combined with a ¼ wave plate is disposed at the side of a diffused light side, while, in a light path which causes light transmitted through the object to form an image on the photoelectric detector 6 through the lens, a detecting side circular polarizer which includes a ¼ wave plate and a plane polarizing plate is placed. An output electric signal of the photoelectric detector is subjected to analog operation processing.

13 Claims, 15 Drawing Figures

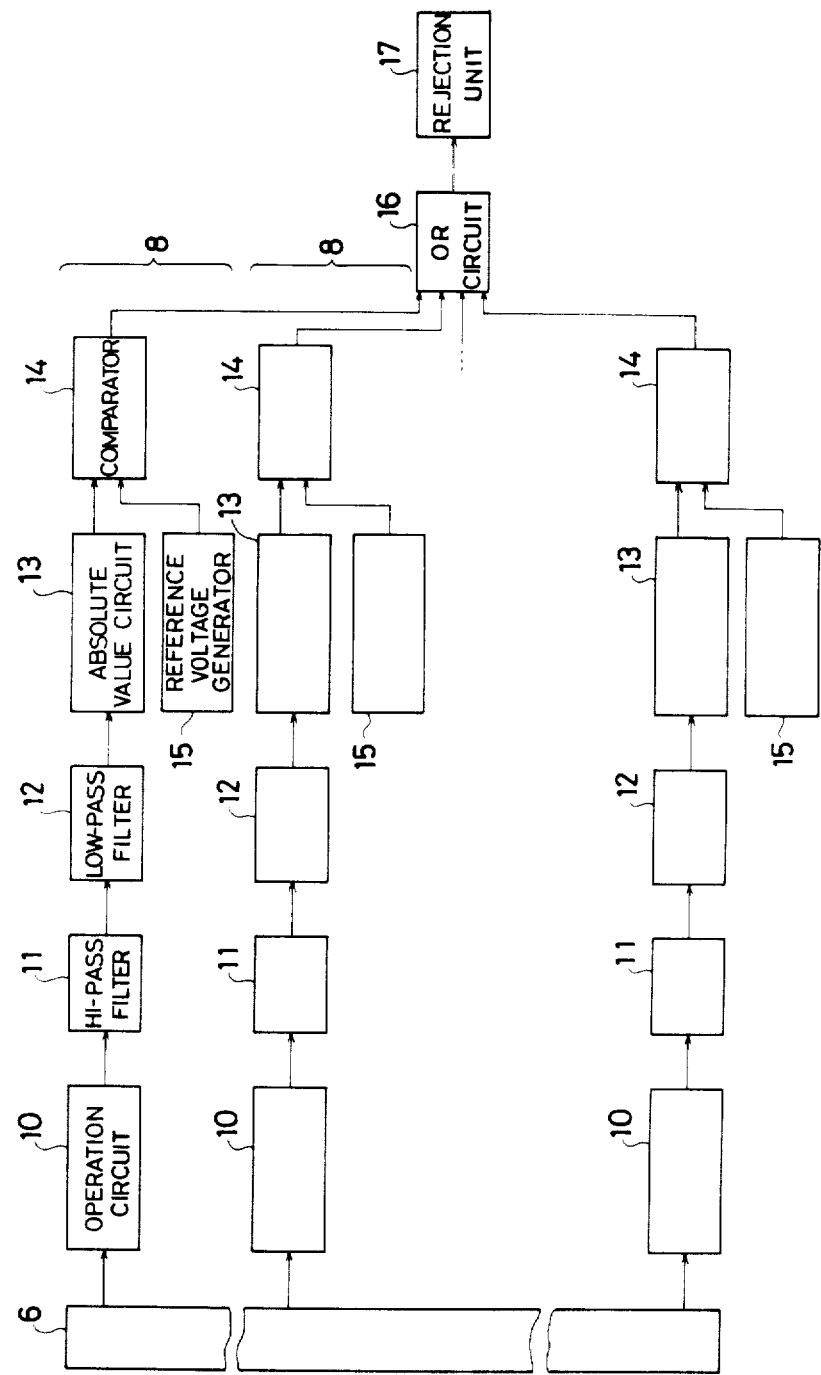

FIG.4
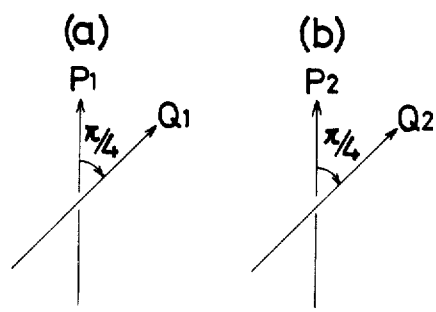
FIG.5
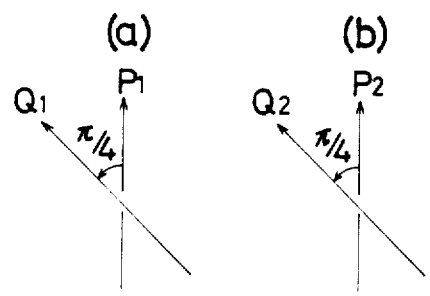
FIG.7 FIG.8 FIG.10
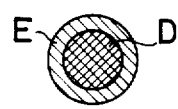
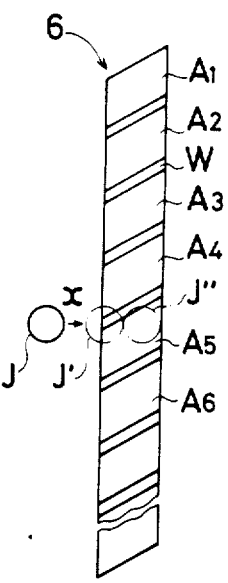

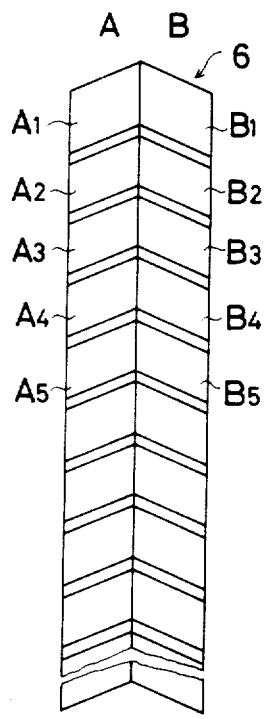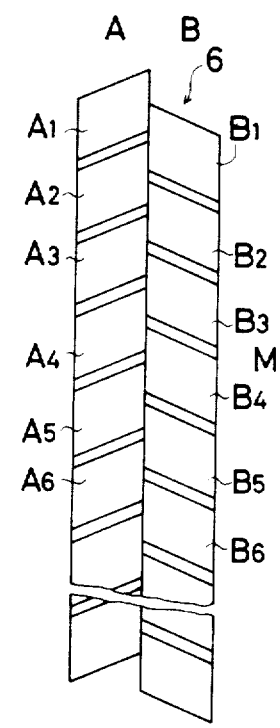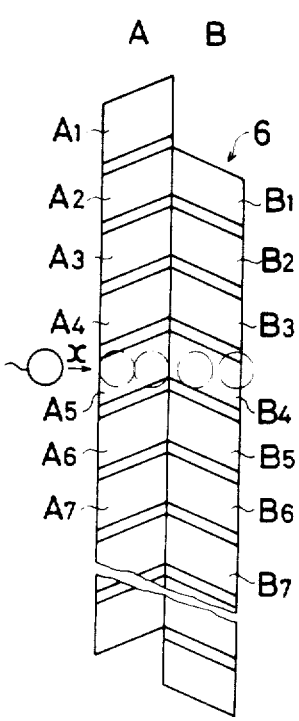

APPARATUS FOR DETECTING FAULTS IN TRANSPARENT OBJECTS

BACKGROUND OF THE INVENTION

The present invention generally relates to an apparatus for detecting faults and more particularly, to a fault detecting apparatus for detecting faults in transparent bodies or objects such as glass bottles and the like.

As apparatuses for effecting fault detection of the above described type, there have conventionally been known one type which adopts the dark-on system, and the other type which is based on the polarized light-on system.

The dark-on system as referred to above is the system arranged to project dark portions corresponding to foreign matters and the like, onto a detecting plane through utilization of a light shielding property of such foreign matters mixed in a raw material of a transparent object to be inspected.

However, in this dark-on system, the items to be inspected are limited to light shielding foreign matters such as pieces of bricks or metals, etc. For example, in the case where the item, to be inspected is a glass bottle, mixing of a foreign matter such as finely crystallized glass material, into the raw material is not permitted due to formation of undesirable strains or distortion, but in the dark-on system as described above, it is impossible to detect such transparent foreign matters. Moreover, in this system, if it is intended to raise the sensitivity so that even very small foreign matters may be detected, seam, satin-like finish, engraving, etc. which should not be regarded as foreign matters, are undesirably detected without being differentiated from the foreign matters, and thus the object is wrongly judged as a faulty item. The arrangements based on the above system are conventionally disclosed, for example, in U.S. Pat. Nos. 3,727,068 and 4,280,624.

On the other hand, the polarized light-on system is the system in which polarizing plates are respectively disposed at a light incident side where light is projected onto the object to be inspected, and also, at a detecting side where light transmitted through the object to be inspected is detected, with main axes of these polarizing plates being set to intersect at right angles to each other (as disclosed in U.S. Pat. No. 3,963,348). In the case where no foreign matters and the like are present in the raw material of the object to be inspected, since the plane polarized light taken out from the incident side polarizing plate is transmitted as it is through the object to be inspected, this transmitted light is shielded by the detecting side polarizing plate so as not to reach the detecting plane. Meanwhile, in the case where foreign matters are present in the raw material to form strains thereat, a plane polarized light component transmitting through the detecting side polarizing plate is formed in the light transmitted through the object to be inspected, by the photoelastic effect at the above strain portion. By detecting such a component on the detecting plane, detection of presence of foreign matters, i.e. the fault detection is to be effected.

However, most of the foreign matters mixed in the raw material are generally free from strains even if they are large in size, and moreover, such foreign matters have a light shielding property in most cases. Accordingly, transmitted light corresponding to the foreign matters can not be detected in almost all cases, and only the transmitted light formed at the peripheral portions of the foreign matters due to strains may be detected somehow. Therefore, the detecting accuracy of the polarized light-on system as described so far is considerably low as compared with that of the dark-on system. If it is intended to raise the detecting accuracy by the polarized light-on system, an expensive photoelectric detector must be employed, with a further necessity for increasing light intensity of a light source, and therefore, it is required to take various countermeasures such as installation of a cooling device to prevent the polarizing plate from melting by heat due to light or provision of a water distribution system, thus resulting in such disadvantages the constructions are undesirably complicated, with consequent inconvenience in handling and difficulty in maintenance, etc.

Apart from the foregoing arrangements, as one example of the dark-on system, it may be so arranged that a pair of plane polarizing plates whose main axes are directed in the same direction, are disposed at front and rear sides of the object to be inspected so that light can be transmitted up to the detecting side only when no foreign matters are present in the object to be inspected, for detection of faults in the transparent bodies. In the above case, however, troublesome procedures are required for the setting to align the main axes of the plane polarizing plates, while any sufficiently favorable result has not been available thereby, either.

SUMMARY OF THE INVENTION

Accordingly, it is a primary object of the present invention to provide an improved fault detecting apparatus for transparent objects, which has a high detecting accuracy through simple constructions so as to substantially eliminate the drawbacks inherent in the conventional apparatuses of this kind.

According to the present invention, there is provided a system characterized in the following points.

More specifically, the fault detecting apparatus for transparent objects according to the present invention is so arranged that, by projecting a diffused light towards an object to be inspected, light transmitted through the object to be inspected is formed into an image through a lens system so as to convert the optical image into an electrical signal by a photoelectric detector disposed on an image forming surface for judging a quality of the object to be inspected by subjecting the electric signal to a signal processing system, and is characterized in that there are provided incident side circular polarizer which includes a polarizing plate combined with a ¼ wave plate and is disposed between the diffused light source and the object to be inspected so as to receive the diffused light by the polarized plate directed towards a side of the light source for taking out a monochromatic light corresponding to the ¼ wave plate from a side of the ¼ wave plate as circularly polarized light in a predetermined revolving or turning direction, and a detecting side circular polarizer which includes a ¼ wave plate combined with a polarizing plate and is disposed between the object to be inspected and the photoelectric detector so as to reveive a circularly polarized light of the light transmitting through the object to be inspected and in the same turning direction as the circularly polarized light at the incident side, by the ¼ wave plate directed towards the side of the object to be inspected for taking out as a plane polarized light from the side of the polarizing plate.

According to the present invention, effects as follows may be obtained based on the principle as described in the foregoing. (a) Instead of detecting the light shielding foreign matters mixed in the object to be inspected as dark portions as they are as in the conventional dark-on system, dark portions corresponding to strain portions adjacent the foreign matters are formed around the dark portions by the foreign matters, in addition to the dark portions corresponding to the foreign matters themselves, and therefore, the area of the dark portions detected as a defective image is increased as compared with that of the conventional case, with a consequent marked improvement of the detecting accuracy. (b) Although the transparent foreign matters such as fine crystallized glass, etc. could not be detected in the conventional dark-on system, such transparent foreign matters as the fine crystallized glass as above may be readily detected as faulty images constituting the dark portions according to the detecting apparatus of the present invention, and moreover, since the foreign matters without strains can be detected in the similar manner as in the conventional dark-on system, the range of foreign matters that can be detected may be enlarged to a large extent. (c) Meanwhile, seam, satin-like finish, and engraving, etc. on the surface of a glass bottle and the like should not be detected as faults, and according to the fault detecting apparatus of the present invention, such transparent portions without strains are not detected as faults, and thus, the inconvenience of wrongly judging good products as faulty products may be avoided.

These and other objects and features of the present invention will become apparent from the following description.

BRIEF DESCRIPTION OF THE DRAWINGS

FIG. 2 is a block diagram which illustrates a signal processing system thereof, FIGS. 4(a) and 4(b) are diagrams explanatory of the relation between main axes of circular polarizers respectively, FIGS. 5(a) and 5(b) are also diagrams explanatory of another relation between main axes of the circular polarizers, FIGS. 7 and 8 are diagrams respectively showing faulty images, FIG. 10 is a schematic front elevational view showing a specific example of a photoelectric detector according to a second embodiment of the present invention, and FIGS. 11 to 15 are schematic front elevational views respectively showing specific examples of photoelectric detectors according to a third embodiment of the present invention.

DETAILED DESCRIPTION OF THE PREFERRED EMBODIMENT

Figure 1:
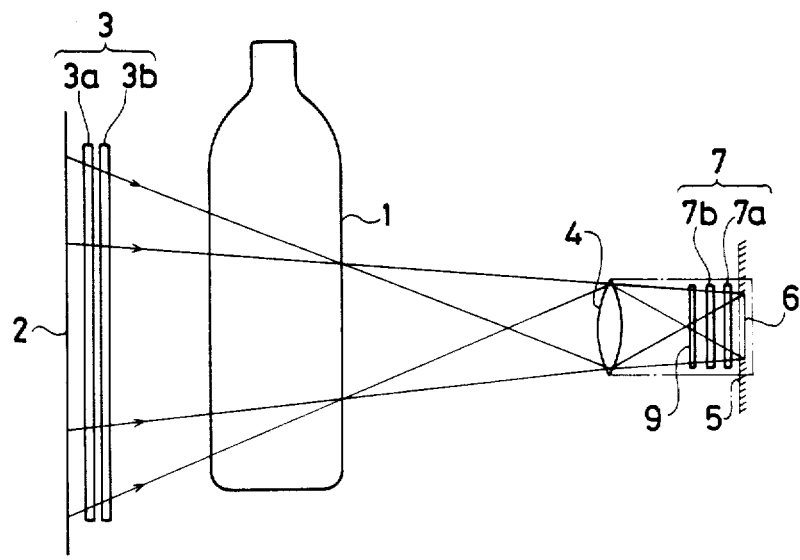
FIG. 1 is a schematic diagram for explaining one preferred embodiment of the present invention.

Referring now to the drawings, particularly to FIGS. 1 through 8, there is shown in FIG. 1, a fault detecting apparatus for transparent objects according to one preferred embodiment of the present invention, which is intended to inspect glass bottles as objects to be inspected for examining faults at body portions thereof. At an incident side where diffused light is projected from a diffusing plate 2 acting as a diffused light source, towards the object 1 to be inspected, there is disposed an incident side circular polarizer 3 which includes a plane polarizing plate 3a combined with a ¼ wave plate 3b so as to receive the diffused light by the plane polarizing plate 3a directed to the light source side for taking out monochromatic light corresponding to the ¼ wave plate 3b from the side of said ¼ wave plate 3b as a circularly polarized light in a predetermined revolving or turning direction. Meanwhile, at the detecting side arranged to collect light transmitted through the object 1 to be inspected, by a lens system 4 so as to form an optical image which is converted into an electrical signal by a photoelectric detector 6 provided on an imaging plane 5, there is disposed a detecting side circular polarizer 7 which includes a ¼ wave plate 7b similar to the ¼ wave plate 3b at the incident side and combined with a plane polarizing plate 7a so as to receive circularly polarized light of the light transmitted through the object 1 in the same turning direction as the circularly polarized light at said incident side, by the ¼ wave plate 7b directed toward the side of the object 1, for taking out as a plane polarized light from the side of the plane polarizing plate 7a. Thus, the electrical signal produced from the photoelectric detector 6 by the plane polarized light from the polarizer is subjected to analog operation processing at a signal processing system 8 in a subsequent stage, thereby to detect faults in the object 1 to be inspected.

As described earlier, in the case where a right-handed circular polarizer, in which a main axis Q1 of the ¼ wave plate 3b is deviated by $\pi/4$ in the clockwise direction as observed from the side of the ¼ wave plate 3b, with respect to a main axis P1 of the plane polarizing plate 3a positioned at (or facing) the light source side as shown in FIG. 4(a), is employed as the incident side circular polarizer 3, another right-handed circular polarizer, in which a main axis Q2 of the ¼ wave plate 7b is deviated by $\pi/4$ in the clockwise direction as observed from the side of this ¼ wave plate 7b (FIG. 4(b) shows the state as observed from the side of the ¼ wave plate 7b) with respect to a main axis P2 of the polarizing plate 7a facing the side of the photoelectric detector 6, is employed as the detecting side circular polarizer 7. Conversely, in the case where a left-handed circular polarizer, in which the main axis Q1 of the ¼ wave plate 3b is deviated by $\pi/4$ in the counterclockwise direction with respect to the main axis P1 of the plane polarizing plate 3a facing the light source side as shown in FIG. 5(a), is employed as the incident side circular polarizer 3, another left-handed circular polarizer, in which the main axis Q2 of the ¼ wave plate 7b is deviated by $\pi/4$ in the counterclockwise direction with respect to the main axis P2 of the plane polarizing plate 7a as observed from the side of the ¼ wave plate 7b, is employed as the detecting side circular polarizer 7, as in FIG. 5(b) showing the state viewed from the side of the ¼ wave plate 7b.

Although the detecting side circular polarizer 7 is disposed at the position close to the photoelectric detector 6 so as to reduce the influences by thicknesses or setting errors, etc. of the polarizing plate 7a, ¼ wave plate 7b and the like as far as possible, the circular polarizer 7 may be disposed at any position in terms of principle so long as it is located between the object 1 to be inspected and the photoelectric detector 6, and, for example, it may be provided at the forward side of the optical system 4.

Since the ¼ wave plates 3b and 7b of the respective circular polarizers 3 and 7 are adapted to correspond to monochromatic light with a wavelength at 800 nm, it is required to select the monochromatic light having the wavelength of 800 nm from light to be employed for the detection.

Figure 6:
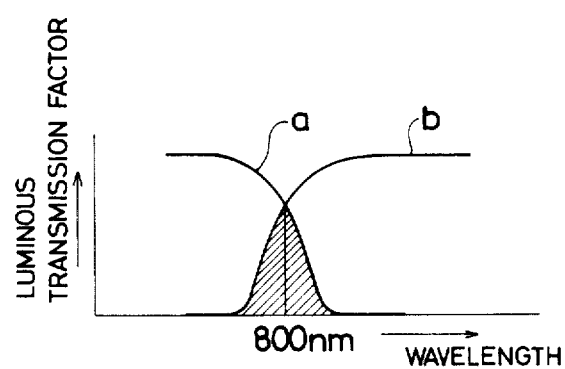
FIG. 6 is a graph showing light filtering characteristics of a monochromatic light filtering structure.

The selection of the monochromatic light as described above may be effected immediately after emission of diffused light from the diffusing plate 2, but in the present embodiment, a wavelength control filter 9 having a light filtering characteristic indicated by "a" in FIG. 6 is disposed in front of the detecting side circular polarizer 7. Simultaneously with the above, an infrared polarizing plate having a light filtering characteristic as shown by "b" in FIG. 6 is employed as the polarizing plate 7a of the detecting side circular polarizer 7 for setting so that the monochromatic light having the wavelength of approximately 800 nm may be filtered at the detecting side.

Since light filtered in such an arrangement as described above is not of monochromatic light in the strict sense of the word, but is light having a certain band width with respect to the wavelength of 800 nm as a center as indicated by hatching in FIG. 6, correct circularly polarized light only can not be derived, with the light having a tendency towards elliptically polarized light to a certain extent. However, the elliptically polarized light to such a degree does not affect the detecting accuracy so much, and a band width to some extent may be provided without any inconvenience. Moreover, light intensity sufficient for the detection may be obtained thereby. It is to be noted here that the wavelength control filter 9 need not necessarily be provided in front of the ¼ wave plate 7b, but may be disposed at any position from the light source up to a position immediately before the photoelectric detector 6, and if the filtration of monochromatic light is effected at the detecting side, it is possible to avoid the influence by the disturbing light which may possibly be incident upon a light path.

Figure 3:
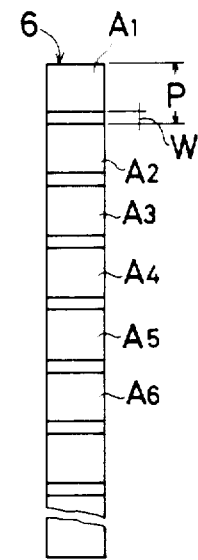
FIG. 3 is a schematic front elevational view showing a specific example of a photoelectric detector.

As shown in FIG. 3, the photoelectric detector 6 comprises a photodiode array in which a plurality of rectangular unit elements A1, A2, . . . and An are aligned. The respective unit elements A1, A2, . . . and An are arranged, for example, at a pitch of 1.5 mm, with a blind or non-sensitive zone width set at 0.3 mm, and such blind zone width is set as narrow as possible.

In the present embodiment to be applied to the inspection of barrel portions of glass bottles, the longitudinal direction of the photodiode array is aligned with the direction of height of the glass bottle which is the object 1 to be inspected.

The object 1 is subjected to light scanning for inspection by being rotated.

The signal processing system 8 includes a operation circuit 10 which subjects the electric signal produced from the photoelectric detector 6 to analog operation processing, a high-pass filter 11 which eliminates low frequency signals from an output of the operation circuit 10, a low-pass filter 12 which eliminates high frequency signals from an output of the high pass filter 11, an absolute value circuit 13, a comparator 14 for comparing an output of this circuit with a predetermined reference voltage, and a reference voltage generator 15 which imparts said reference voltage.

Subsequently, functions of the fault detecting apparatus as explained so far will be explained hereinbelow.

At the incident side circular polarizer 3, the circularly polarized light in the predetermined turning direction is derived upon reception of the diffused light emitted from the diffusing plate 2. This circularly polarized light is projected onto the barrel portion of the glass bottle which is the object 1 to be inspected. In the absence of foreign matters in the material of the object 1 to be inspected, the circularly polarized light thus projected passes through the object 1 as it is. Since the incident side circular polarizer 3 and the detecting side circular polarizer 7 are disposed so that the respective ¼ wave plates 3b and 7b confront each other, the circularly polarized light transmitting through the object 1 is received by the detecting side circular polarizer 7 so as to be taken out from the side of the polarizing plate 7a as a plane polarized light. In other words, in the case where no foreign matters are mixed in the object 1 to be inspected, light is transmitted through up to the photoelectric detector 6.

On the contrary, in the case where foreign matters are mixed in the raw material of the object 1 to be inspected to provide the light shielding property thereby, light striking against the foreign matters is not transmitted irrespective of the circularly polarized light transmitting function, in the case of the detecting side circular polarizer 7, and at the imaging plane where the photoelectric detector 6 is disposed, the portion corresponding to the foreign matter is formed into an image of dark portion as shown at a symbol D in FIG. 7.

On the other hand, in the case where strain is formed at the peripheral portion of the foreign matter in the object 1 to be inspected due to mixing of such foreign matter, the circularly polarized light projected onto the object 1 from the incident side is subjected to double refraction by the photoelastic effect of the strain portion so as to be transmitted through the object 1 to be inspected. Since light leaving the object 1 is deviated from the circularly polarized light to the elliptic polarized light according to the degree of the strain, light transmission is obstructed at the detecting side circular polarizer 7 according to the degree of said strain, and at the imaging plane, as shown by a symbol F in FIG. 7, the peripheral portion of the dark portion D is surrounded by the dark portion corresponding to the strain portion. Accordingly, as compared with the dark portion D corresponding to the foreign matter itself as obtained in the conventional dark-on system, the dark portion area to be detected is increased by the amount of a dark portion E corresponding to the strain portion, with a consequent improvement of the detecting accuracy.

In the case where the fine crystallized glass is mixed into the raw material in the present embodiment in which the object 1 to be inspected is of a glass bottle, the mixing of such fine crystallized glass should be judged as a fault in the similar manner as in the mixing of foreign matters. In the above case, the circularly polarized light incident upon the object 1 to be inspected is subjected to double refraction by the fine crystallized glass. Therefore, the light leaving the object 1 is prevented in its transmission by the detecting side circular polarizer 7 acoording to the degree of the state of melting of the fine crystallized glass, and at the imaging plane, the dark portion corresponding to the fine crystallized glass is formed as shown by a symbol F in FIG. 8.

In the photoelectric detector 6 composed of the photodiode array, the light signal is converted into an electrical signal, which is subjected to the analog operation processing in the operation circuit 10 at the subsequent stage.

On the assumption that respective outputs of the unit elements A1, A2 ... and An arranged in one row to constitute the photodiode array in FIG. 3, are represented by EA1, EA2, EA3 ... and EAn, the opration processing for |EAn−EAn+1|(n=1, 2, 3 ...) is effected at the operation circuit 10, and thus, lines at the seams of the glass bottle mold, etc. where the image is extended through in a longitudinal direction with respect to the photodiode array, are erased, i.e. are not detected, since the relation becomes |EA−EA2|=O, |EA2−EA3|=O, ... |EAn−EAn+1|=O.

The output signal of the operation circuit 10 is applied to the high-pass filter 11, in which, for example, influences due to thickness variation at the bottle barrel portions, linear patterns extending over long lengths in the circumferential direction, etc. may be eliminated. More specifically, the thickness variation constitutes low frequency waves in itself, while the images due to the linear patterns extending over long lengths in the circumferential direction, or due to some seams, are formed long with respect to the diode array in such a manner as to cross it, and therefore, the waveforms thereof constitute low frequency waves. Accordingly, by preliminarily arranging to cut low frequency waves lower than a predetermined level, such influences due to thickness variations, lines, stripes, etc. which are not of faults may be eliminated. Subsequently, the output from the high-pass filter 11 is applied to the low-pass filter 12, in which the influence by the satin-like pattern on the surface of the bottle may be eliminated. This is based on the principle that, in the case of the satin-like pattern, the image thereof is small and formed at short intervals, the output waveform at such portion constitutes high frequency waves. The signal from the low-pass filter 12 is further applied to the comparator 14 through the absolute value circuit 13. At this comparator 14, the signal is compared with the reference voltage from the reference voltage generator 15 so as to produce an rejecting signal. By arranging the reference voltage from the above reference voltage generator 15 variable, the sensitivity can be properly adjusted. The output from the comparator 14 is applied to the OR circuit 16, from which the last rejecting signal is applied to an rejector 17 for the glass bottle.

Figure 9:
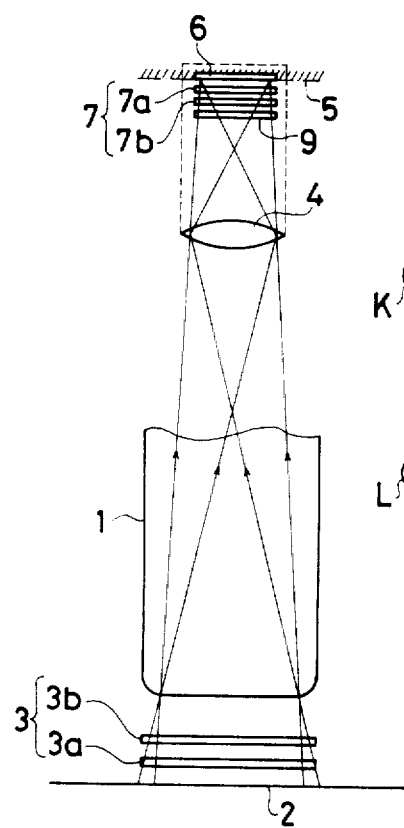
FIG. 9 is a schematic diagram showing another arrangement for detection.

In the foregoing embodiment, description has been made with reference to the case where faults at the barrel portions of the glass bottle as the object 1 to be inspected are examined, but in the case where faults at bottom portions of glass bottles are to be inspected as shown in FIG. 9, it may be so arranged that, with the diffused light being projected from the vicinity of the bottom portion, the incident side circular polarizer 3 and the detecting side circular polarizer 7, etc. are disposed in the longitudinal direction of the glass bottle. In this case, the diode array constituting the photoelectric detector 6 may be aligned, in its longitudinal direction, with the radial direction in the bottom of the glass bottle.

Referring now to FIG. 10, a second embodiment according to the present invention will be described hereinafter.

In the fault detecting apparatus of the second embodiment as shown in FIG. 10, the construction of the photoelectric detector 6 in the first embodiment is so modified that each of the unit elements A1, A2, ... and An for the photodiode array is formed into a parallelogram, with corresponding one side thereof being aligned on the same straight line, so that the blind zone W is inclined at a predetermined angle with respect to the passing direction X of a fault image J, thereby to reduce the influence by the blind zone W.

In FIG. 10, when the explanation is given with reference to the case where the fault image J passes through the diode array 6 in the direction indicated by an arrow X, the output |EA4−EA5| has a value close to zero when the fault image J is located at the position J', but upon arrival of the fault image J at a position J'', the output |EA4−EA5| takes a value approximately corresponding to the area of the fault image J, and thus, the influence of the blind zone W may be reduced.

Since other constructions of the second embodiment are generally similar to those of the first embodiment, detailed description thereof are abbreviated for brevity.

Referring further to FIGS. 11 through 15, a third embodiment according to the present invention will be described hereinbelow.

Figure 11:
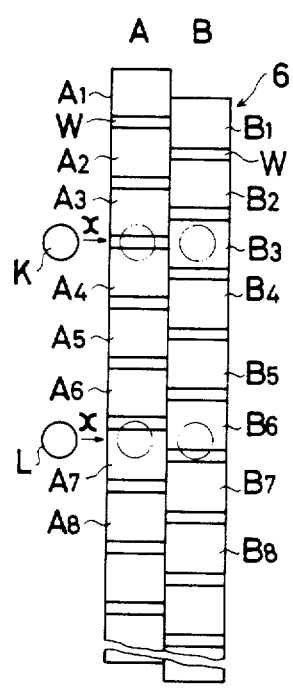

In the fault detecting apparatus of the third embodiment, the constructions of the photoelectric detector 6 in the first embodiment is modified in such a manner that the respective unit elements A1, A2, ... and An for the diode array are provided in two rows as shown. In this case, it is preferable to arrange rows A and B, through deviation, for example, by half a pitch. In the example of FIG. 11, in the case where a fault image K passes through the diode array in the direction of an arrow X, the output |EA2−EA3|, |EA3−EA4|, |EA4−EA5| in the row A takes a value considerably lower than the output corresponding to the area of the fault image K, but meanwhile, the output |EB2−EB3|, |EB3 −EB4| in the row B becomes a value corresponding to the area of the fault image K, thus making it possible to eliminate the influence of the blind zone W. It is to be noted, however, that, in the case where the fault image represented by a symbol L pass through in the direction of the arrow X, both of the outputs |EA6−EA7|, |EA7−EA8| and |EB5−EB6|, |EB6−EB7| are less than the output corresponding to the area of the fault image L, and a slight influence of the blind zone W may be present. As examples for preventing the influence of the blind zone W, diode arrays as shown in FIGS. 12 through 15 may be considered besides the example of FIG. 11 as described above.

Figure 12:
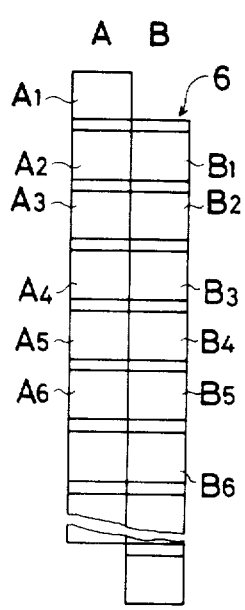

FIG. 12 shows the diode array in which the row A and row B are deviated by one pitch. FIG. 13 shows another photodiode array in which parallelogram unit elements A1, A2 ... B1, B2 ... are symmetrically arranged in two rows. In this arrangement of FIG. 13, the unit elements A1, A2 ... for the row A and the unit elements B1, B2 ... for the row B are arranged in the symmetrical relation with each other in order to prevent deviations of singals due to inclining directions of slantwise faults. In the arrangement of FIG. 14, the unit elements A1, A2 ... B1, B2 ... in the parallelogram are deviated by half a pitch between the row A and row B, while in the arrangement of FIG. 15 also, the unit elements are deviated by one pitch between the row A and row B.

As described so far, for preventing the influence of the blind zone W, there are available such means as the narrowing the width of the blind zone W itself, forming unit elements A1, A2 ... into parallelograms, and employing two rows, but as a means for reducing the number of appliances such as amplifiers, etc. required for the inspection, it is possible to effect processings as stated hereinbelow.

More specifically, only for detecting the faults, the analog calculation formulas may be in the form of $|EA1-EA2|$, $|EA2-EA3|$, $|EA3-EA4|$, ... $|EAn-EAn+1|$, $|EB1-EB2|$, $|EB2-EB3|$ ... $|EBn-Esn+1|$ for each row between the upper and lower unit elements, but in this case, the signal processing system 8 is required in the number equivalent to the number of the unit elements, with a plurality of processing appliances being required for each of such signal processing systems 8. Moreover, in the case where amplification or the like is required for each of the processing appliances, the number of amplifiers equivalent to the number of processing appliances X the number of unit elements is required, and thus, the resultant apparatus becomes bulky to occupy a large space, and tends to be expensive. Accordingly, in the present embodiments, it has been so arranged that the analog operation is effected among four adjacent unit elements between the two rows A and B of the diode array. For the analog operation expression, there may be employed, for example, such expression as $|(EAn+EBn)-(EAn+1+EBn+1)|(n=1, 3, 5 ...)$, $|(EAn+EBn+1)-(EAn+1-EBn)|(n=1, 3, 5 ...)$.

Now, as an actual example, the expression $|(EAn+EBn)-(EAn+1+EBn+1)|$ is applied to the photodiode array shown in FIG. 15 for explanation of the case in which a fault image M passes through the photodiode array in the direction of the arrow X. The output $|(EA1+EB1)-(EA2+EB2)|$ is zero, and the output $|(EA3+EB3)-(EA4+EB4)|$ takes a value in which the waveform peak corresponds to the area of the fault image M. Furthermore, the output $|(EA5+EB5)-(EA6+EB6)|$ also takes a value corresponding to the area of the fault image M. Meanwhile, even when the fault image M passes through other positions, any of the outputs takes a value corresponding to the area of the fault image M, and in such a case, the number of required calculations may be ¼ of the number of the unit elements.

As still another embodiment, there is shown a case in which the expression $|(EAn+EBn+1)-(EAn+1+EBn)|$ $(n=1, 3, 5 ...)$ is applied to the diode array of FIG. 11. In the first place, when the fault image K passes through the diode array in the direction of the arrow X, the output $|(EA1+EB2)-(EA2+EB1)|$ is zero, and the output $|(EA3+EB4)-(EA4+EB3)|$ corresponds, in the waveform peak thereof, to the area of the fault image K. Meanwhile, in the case where the fault image L moves in the direction of the arrow X, the output $|(EA5+EB6)-(EA6+BB5)|$, and the output $|(EA7+EB8)-(EA8+EB7)|$ correspond to the area of the fault image L. The same state also applies to the case where the fault images K and L pass through other positions.

Even in these cases, the number of required calculations may be only ¼ of the number of unit elements. Of course, by the analog operation among these four unit elements, some errors may be involved from the output corresponding to the area of the fault image, but a considerably high accuracy may be achieved thereby. For example, in the case where the analog operation expression $|(EAn+EBn)-(EAn+1+EBn+1)|$ $(n=1, 3, 5 ...)$ is employed for the diode array of FIG. 15, the range of errors was within approximately ±20% theoretically, and less than ±10% in the data due to factors in the electrical characteristics of the filters 11 and 12. The diode arrays as shown in FIGS. 12 and 13 are not very good in terms of accuracy.

The reason why the number of required operation may be ¼ of the number of the unit elements is such that, by employing unit elements located in the deviated positions between the rows A and B for the four unit elements related to the analog operation, the output corresponding to the area of the fault image may be obtained without effecting a duplicated operation. Moreover, as another method for use, it may be so arranged that, in the photodiode array in which the number of unit elements is arranged in two rows, subtraction is effected betwene the unit element outputs at the left and right sides. Such a method is effective, for example, in the case where one side of the neighboring unit elements is used as a dummy so as to prevent the influence due to thickness variation, e.g. in the circumferential direction of a bottle.

By the arrangement as described above, only one signal processing system 8 per four unit elements becomes sufficient for the purpose, and thus, the respective appliances constituting the signal processing system 8 may be reduced to ¼ in number.

Moreover, in the case where, for example, the total number of amplifiers to be used for the respective appliances in each of the signal processing system 8 is represented by m, the amplifiers nm-nm/4, i.e. 3 nm/4 pieces may be reduced according to the present invention as compared with the conventional arrangements. The above value of 3 nm/4 is very large. Furthermore, by employing swithing elements, it is possible, for example in FIG. 2, to process the path after the high-pass filter 11 in a single row. In the above case, however, it is necessary to employ appliances of high sensitivity which are quick in response.

It is to be noted here that the arrangement as in each of the foregoing embodiments in which the photodiode array is employed as the photoelectric detector 6 may be replaced by a TV camera or a self-scanning type diode array camera. Such a TV camera is not limited to one in which an image pickup portion is composed of a vacuum tube, but may of course be one constituted by a solid state image pickup element such as CCD.

By the foregoing description, it will be clear that the present invention is capable of accomplishing the. objects and effects as described previously.

Furthermore, so far as the positional relation between the incident side circular polarizer (P1+Q1) and the detecting side circular polarizer (P2+Q2) as shown in FIGS. 4 and 5 is maintained, the positional relation of the main axis P1 and P2 between the polarizing plates, i.e. the relation of the main axis angles between the polarizing plate of the incident side circular polarizer and the plane polarizing plate of the detecting side circular polarizer may be set in any way, and therefore, there are such features that the setting and maintenance of the apparatus are readily effected, with a simultaneous convenience in handling.

I claim:

1. An apparatus for detecting faults in transparent objects which is so arranged that by projecting diffused light towards the object to be inspected, light transmitted through said object is formed into an image through a lens system so as to convert the optical image into an electric signal by a photoelectric detector provided on the image forming plane for subjecting said electric signal to a signal processing system, thereby to judge quality of said object to be inspected, said fault detecting apparatus comprising an incident side circular polarizer which includes a plane polarizing plate combined with a ¼ wave plate and is disposed between the diffused light source and the object to be inspected so as to receive the diffused light by the polarized plate directed towards a side of the light source for deriving monochromatic light corresponding to the ¼ wave plate from a side of the ¼ wave plate as circular polarized light in a predetermined turning direction, and a detecting side circular polarizer which includes a ¼ wave plate combined with a polarizing plate and is disposed between the object to be inspected and the photoelectric detector so as to receive a circular polarized light of the light transmitting through said object and in the same turning direction as the circular polarized light as the incident side, by the ¼ wave plate directed towards the side of the object to be inspected for deriving as a plane polarized light from the side of the plane polarizing plate.

2. An apparatus as claimed in claim 1, wherein said photoelectric detector is of a photodiode array in which a plurality of unit elements are aligned, with a blind zone width therebetween being narrowed, said signal processing system including a operation circuit for effecting analog operation between the neighboring unit elements.

3. An apparatus as claimed in claim 2, wherein said photodiode array has its unit elements each in the form of a parallelogram, and arranged in one row so that corresponding one side of each of the unit elements is aligned on the same straight line.

4. An apparatus as claimed in claim 2, wherein said photodiode array has its unit elements arranged in two rows.

5. An apparatus as claimed in claim 4, wherein said photodiode array has its unit elements each in the form of a parallelogram, and so arranged that corresponding one side of each of the unit elements is aligned on the same straight line.

6. An apparatus as claimed in claim 4, wherein the unit elements are positionally deviated between the two rows.

7. An apparatus as claimed in claim 2, wherein the analog operation processing is arranged to be effected each between the respective outputs of upper and lower neighboring two unit elements.

8. An apparatus as claimed in claim 4, wherein the analog operation processing is arranged to be effected each between the respective outputs of left and right neighboring two unit elements.

9. An apparatus as claimed in claim 4, wherein said analog operation processing is arranged to be effected without duplication for each upper and lower and left and right neighboring four unit elements.

10. An apparatus as claimed in claim 9, wherein said analog operation processing is effected in such a manner that the result of subtraction between the upper and lower unit element outputs for each row is subjected to addition.

11. An apparatus as claimed in claim 1, wherein said photoelectric detector is a TV camera.

12. An apparatus as claimed in claim 11, wherein said TV camera employs a solid state image pickup element.

13. An apparatus as claimed in claim 1, wherein said photoelectric detector is a self-scanning type diode array camera.

* * * * *